United States Patent
Henry et al.

(10) Patent No.: US 11,602,407 B2
(45) Date of Patent: Mar. 14, 2023

(54) DEPTH GAUGES AND RELATED METHODS

(71) Applicant: Ascension Texas, Austin, TX (US)

(72) Inventors: Steven L. Henry, Austin, TX (US); C. Kenneth French, Austin, TX (US)

( * ) Notice: Subject to any disclaimer, the term of this patent is extended or adjusted under 35 U.S.C. 154(b) by 0 days.

(21) Appl. No.: 15/699,252

(22) Filed: Sep. 8, 2017

(65) Prior Publication Data

US 2018/0214234 A1 Aug. 2, 2018

Related U.S. Application Data

(60) Provisional application No. 62/385,007, filed on Sep. 8, 2016.

(51) Int. Cl.
*A61B 90/00* (2016.01)
*A61B 5/00* (2006.01)

(52) U.S. Cl.
CPC .......... *A61B 90/06* (2016.02); *A61B 5/4504* (2013.01); *A61B 2090/062* (2016.02)

(58) Field of Classification Search
CPC .............. A61B 90/06; A61B 2090/061; A61B 2090/062; B25B 31/005
USPC ........................................................ 606/102
See application file for complete search history.

(56) References Cited

U.S. PATENT DOCUMENTS

| | | | |
|---|---|---|---|
| 3,738,355 A * | 6/1973 | Salvatore | A61C 19/04 |
| | | | 606/102 |
| 4,016,867 A * | 4/1977 | King | A61B 1/303 |
| | | | 33/512 |
| 4,204,548 A * | 5/1980 | Kurz | G01B 5/14 |
| | | | 600/591 |
| 7,134,216 B2 | 11/2006 | Rupp et al. | |
| 7,165,336 B2 | 1/2007 | Kim | |
| 7,607,238 B2 | 10/2009 | Kim et al. | |
| 8,308,662 B2 | 11/2012 | Lo | |
| 2006/0224161 A1 | 10/2006 | Bhattacharyya | |
| 2009/0171358 A1* | 7/2009 | Chang | A61B 90/06 |
| | | | 606/62 |
| 2013/0096565 A1 | 4/2013 | Fritzinger | |
| 2013/0138106 A1 | 5/2013 | Kumar | |

* cited by examiner

*Primary Examiner* — Amy R Sipp
(74) *Attorney, Agent, or Firm* — Norton Rose Fulbright US LLP

(57) ABSTRACT

This disclosure includes surgical depth gauges and related methods. Some gauges have a probe assembly including a probe having proximal and distal ends, the distal end including one or more prongs, each having a distal-most tip, being movable between a retracted position and a deployed position in which the tip is farther from a longitudinal axis of the probe than when the prong is in the retracted position, and being biased toward the deployed position. Some probe assemblies include a cannula having proximal and distal ends, where the probe is disposable within the cannula such that moving the distal end of the probe toward and away from the distal end of the cannula causes each of the prongs to move between the retracted and deployed positions. Some depth gauges include a sleeve disposable over the probe assembly.

11 Claims, 8 Drawing Sheets

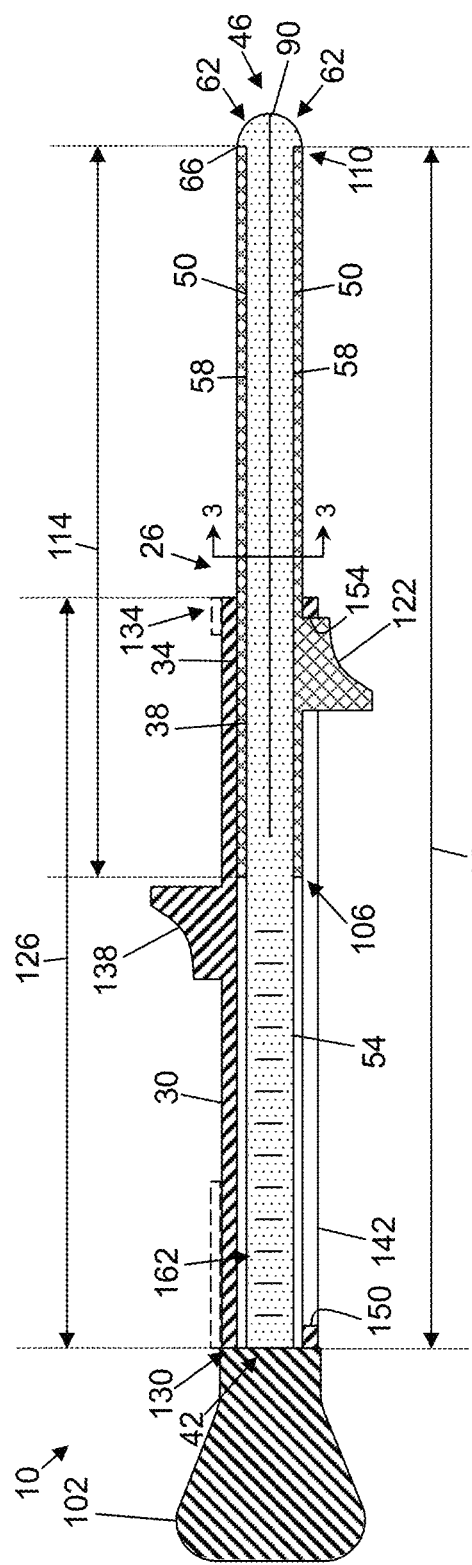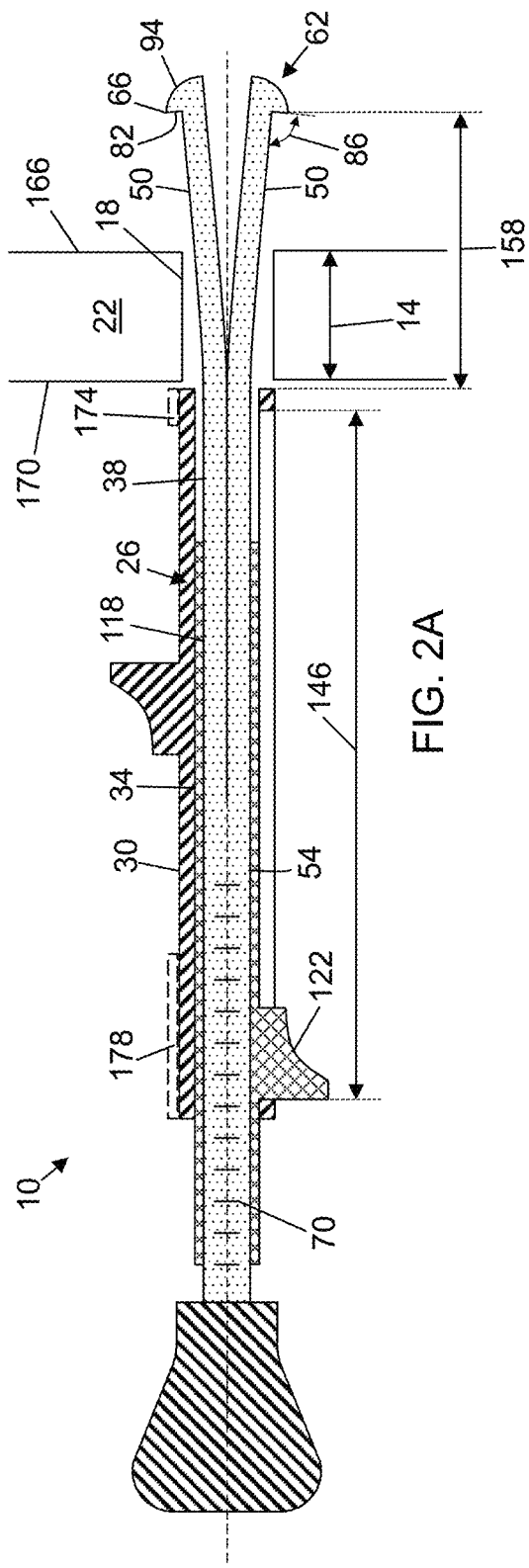

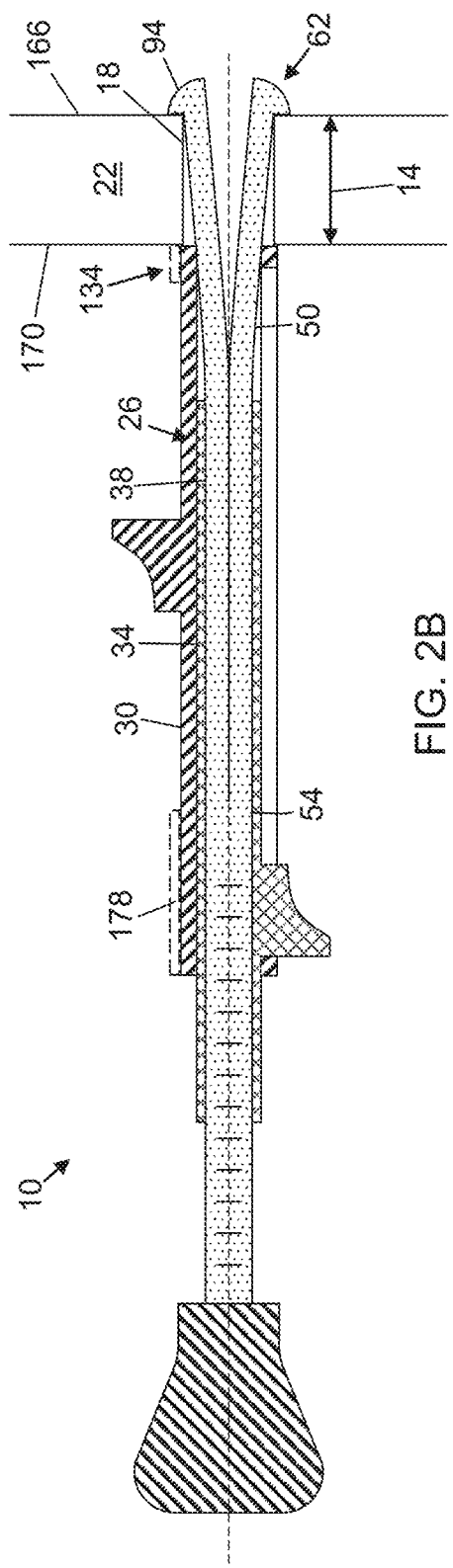
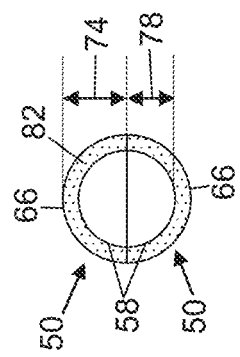
FIG. 2B
FIG. 3

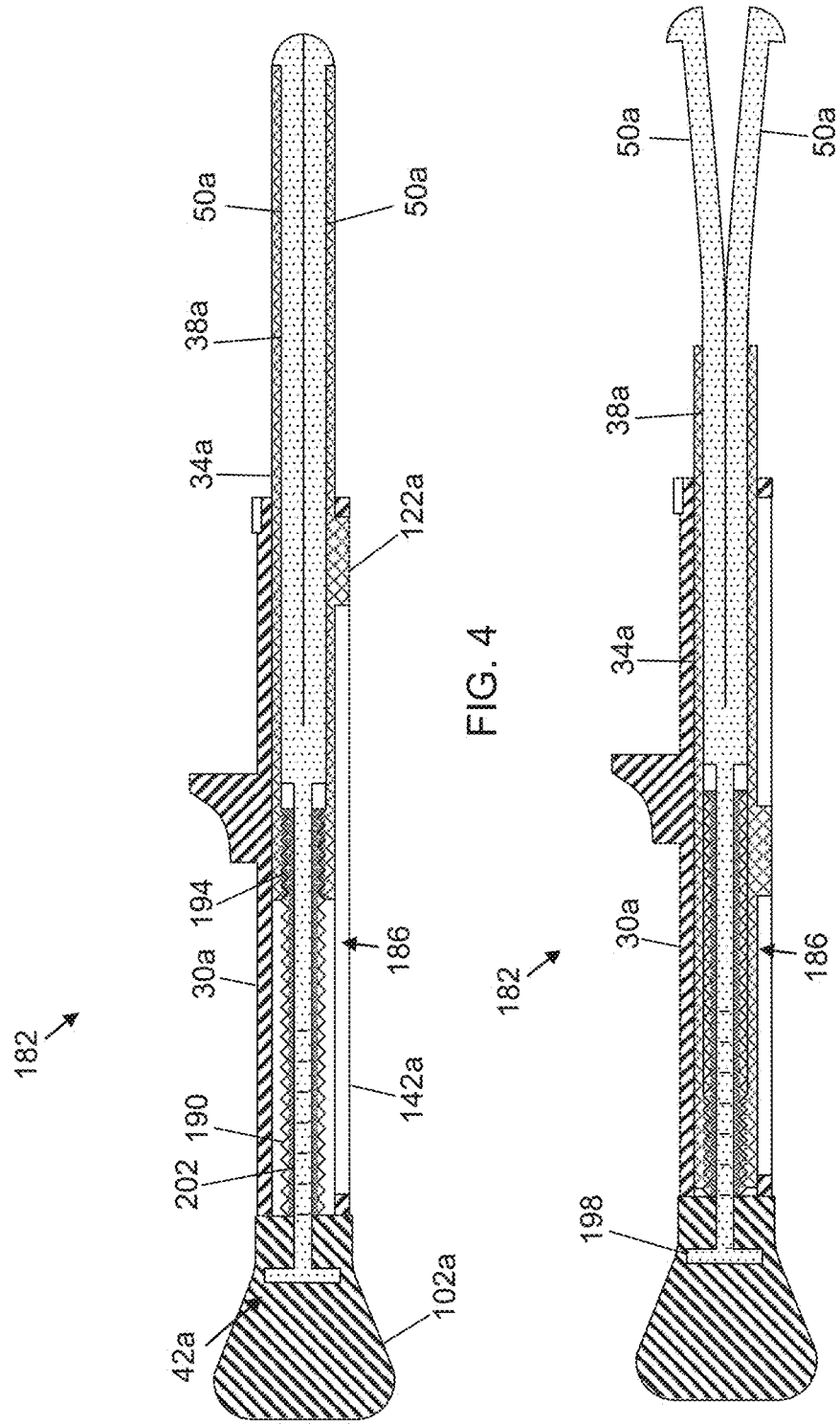

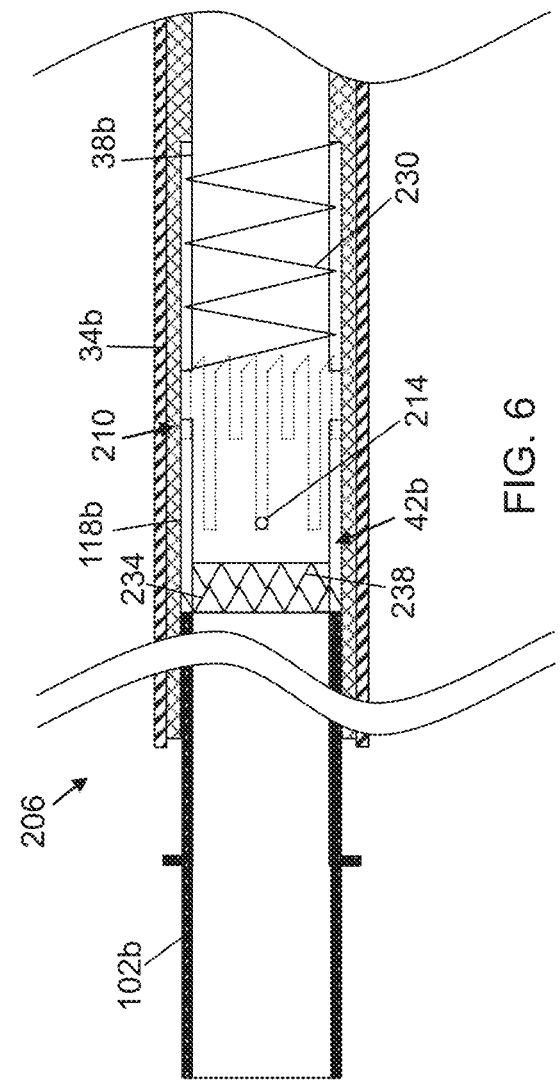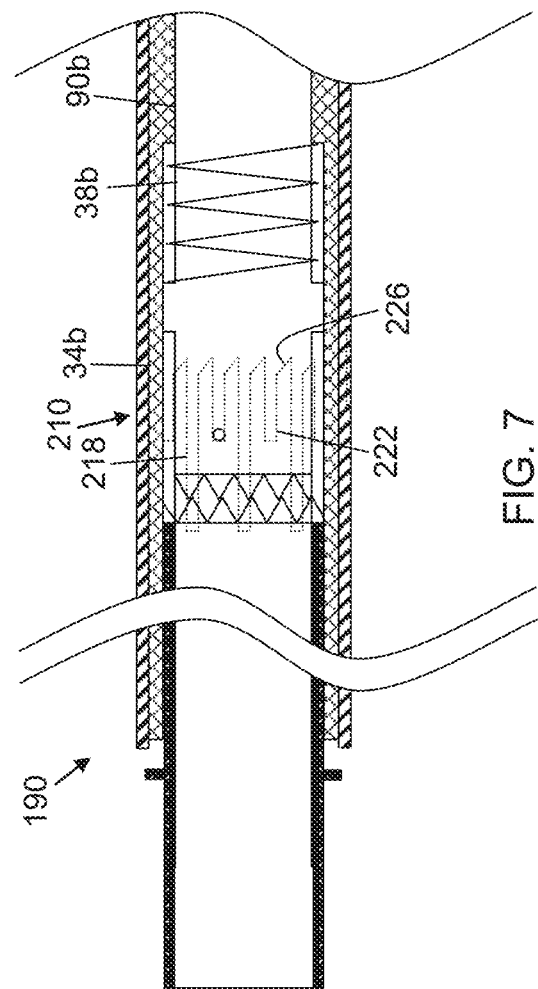

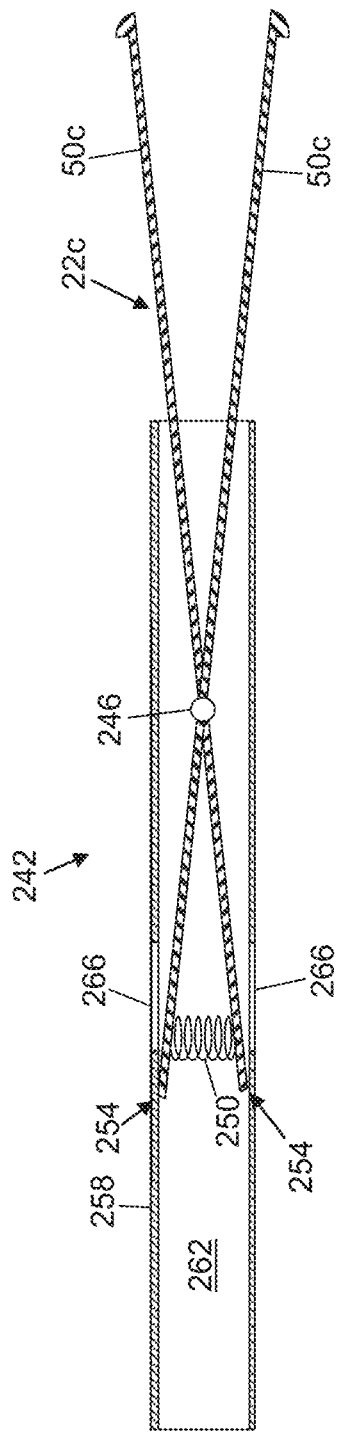

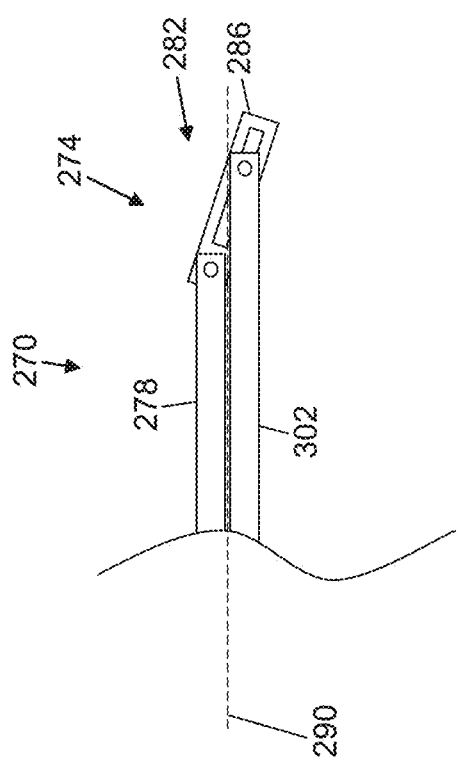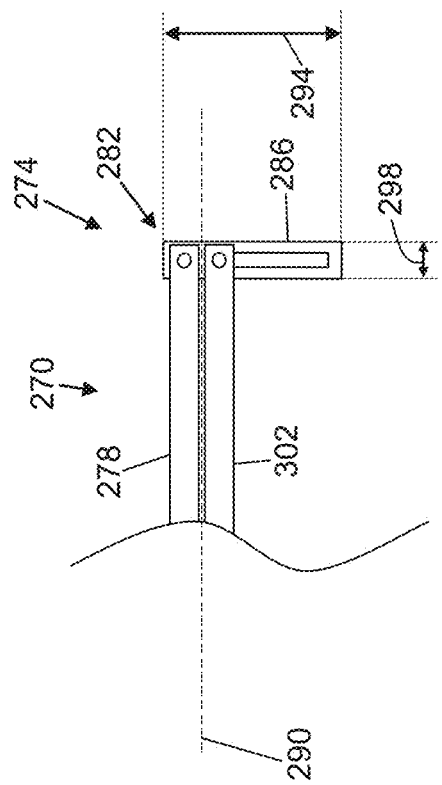

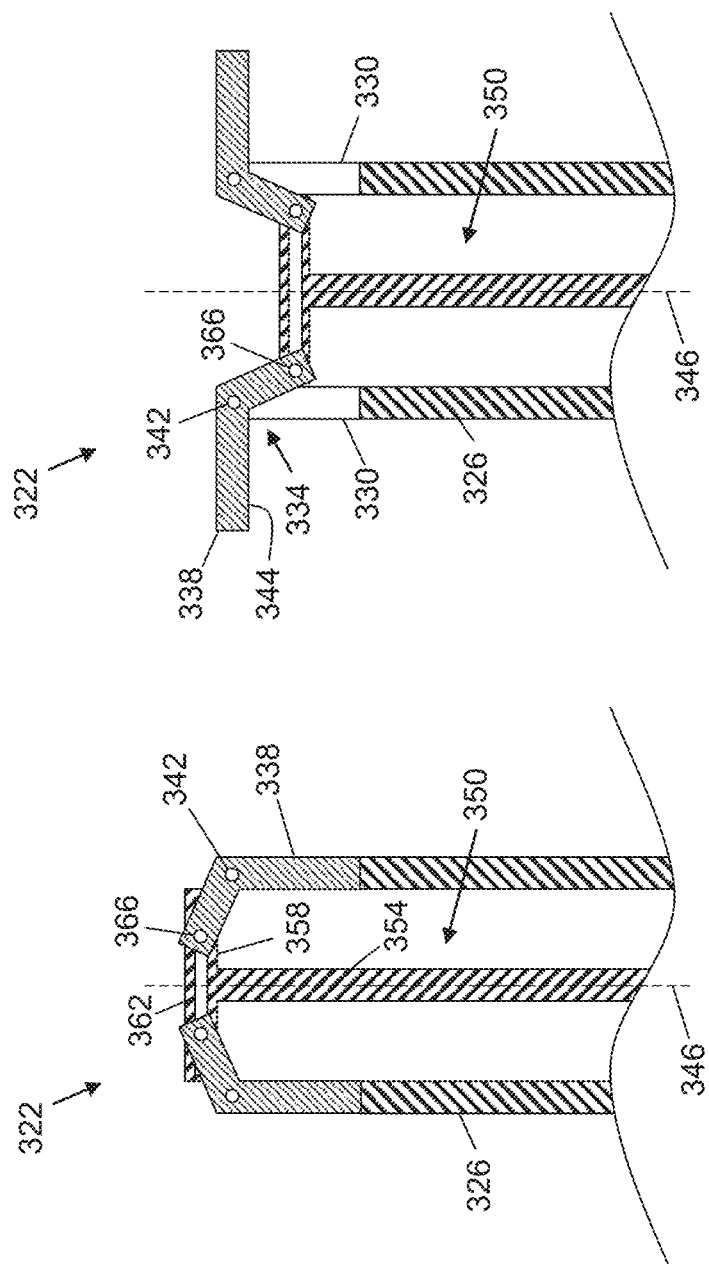

DEPTH GAUGES AND RELATED METHODS

CROSS-REFERENCE TO RELATED APPLICATION

This application claims priority to U.S. Provisional Patent Application No. 62/385,007 filed Sep. 8, 2016, which is incorporated by reference in its entirety.

BACKGROUND

1. Field of Invention

The present invention relates generally to depth gauges, and more specifically, but not by way of limitation, to surgical depth gauges for measuring the depth of a hole in tissue, such as, for example, a bone, and methods for using the same.

2. Description of Related Art

A surgical depth gauge is a measuring device intended for use in various medical procedures. For example, a surgical depth gauge can be used to determine an appropriate screw length for joining a fractured bone. Existing surgical depth gauges may make it difficult to effectively measure a depth of a hole in a tissue, such as a bone, because existing surgical depth gauges may have trouble suitably engaging the tissue.

Examples of depth gauges are disclosed in U.S. Patent Nos.: (1) U.S. Pat. No. 7,134,216; (2) U.S. Pat. No. 7,165,336; (3) U.S. Pat. No. 7,607,238; and (4) U.S. Pat. No. 8,308,662, and U.S. Patent Pub. Nos.: (1) 2006/0224161; (2) 2013/0096565; and (3) 2013/0138106.

SUMMARY

This disclosure includes embodiments of surgical depth gauges and methods (e.g., method for measuring the depth of a hole in a bone). Some embodiments of the present surgical depth gauges comprise: a probe assembly and a sleeve. Some embodiments of the present methods of measuring the depth of a hole in a bone involve the use of one of the present surgical depth gauges to measure the depth of the hole (e.g., by inserting a portion of the surgical depth gauge into the hole).

In some embodiments of the present surgical depth gauges, the probe assembly includes: a probe having a proximal end and a distal end, the distal end including two or more prongs, each having a distal-most tip; where each of the two or more prongs is movable between a retracted position and a deployed position in which the tip of the prong is farther from a longitudinal axis of the probe than when the prong is in the retracted position; and where each prong is biased toward the deployed position. In some embodiments, the sleeve is disposable over the probe assembly such that, when the probe assembly is disposed within a patient's tissue, the sleeve is movable relative to the probe assembly to abut the patient's tissue. In some embodiments, the probe assembly includes a housing; the two or more prongs are at least partially disposed within the housing; and the housing defines one or more openings configured to allow access to at least one of the two or more prongs to permit movement of the prong between the retracted and deployed positions. In some embodiments, the tip of each of the two or more prongs defines a shoulder. In some embodiments, the probe assembly includes a cannula having a proximal end and a distal end; and the probe is disposable within the cannula such that moving the distal end of the probe toward and away from the distal end of the cannula causes each of the two or more prongs to move between the retracted and deployed positions.

In some embodiments of the present surgical depth gauges, the probe assembly includes: a probe having a proximal end and a distal end, the distal end including one or more prongs (each having a distal-most tip; being movable between a retracted position and a deployed position in which the tip of the prong is farther from a longitudinal axis of the probe than when the prong is in the retracted position; and being biased toward the deployed position); and a cannula having a proximal end and a distal end; where the probe is disposable within the cannula such that moving the distal end of the probe toward and away from the distal end of the cannula causes each of the one or more prongs to move between the retracted and deployed positions. In some embodiments, the sleeve is disposable over the probe assembly such that, when the probe assembly is disposed within a patient's tissue, the sleeve is movable relative to the probe assembly to abut the patient's tissue. In some embodiments, the one or more prongs comprises two or more prongs. In some embodiments, the tip of each of the prongs defines a shoulder. In some embodiments, the shoulder of each of the one or more prongs abuts the distal end of the cannula when the prong is in the retracted position. In some embodiments, the distal end of the cannula extends beyond the shoulder of each of the one or more prongs when the prong is in the retracted position. In some embodiments, the shoulder of each of the one or more prongs is disposed in a recess defined by the cannula when the prong is in the retracted position.

Some embodiments of the present surgical depth gauges further comprise: (a) a slider coupled to the probe assembly such that movement of the slider relative to at least one of the probe and the cannula moves the cannula relative to the probe; or (b) a knob coupled to the probe assembly such that rotation of the knob relative to at least one of the probe and the cannula moves the cannula relative to the probe.

In some embodiments of the present surgical depth gauges, the probe is movable relative to the cannula between a first position in which each of the one or more prongs is in the retracted position and a second position in which each of the one or more prongs is in the deployed position; and the probe is biased toward the first position. In some embodiments, the probe assembly comprises one or more releasable catches configured to secure the probe relative to the cannula in at least one of the first and second positions.

In some embodiments of the present surgical depth gauges, at least one of the one or more prongs comprises a resilient material. In some embodiments, at least one of the one or more prongs comprises a cross-section having a circular portion.

In some embodiments of the present surgical depth gauges in which the tip of a (or each) prong defines a shoulder, the shoulder of each of the one or more prongs has a cross-section at its maximum transverse dimension that includes a circular portion.

In some embodiments of the present surgical depth gauges, the probe assembly includes a probe. For example, the prove can have: a proximal end and a distal end; an elongated first body extending to the distal end; and a tip element pivotally coupled to the first body at the distal end, the tip element having a length and a width that is smaller than the length; where the tip element is movable relative to the first body between a first position and a second position in which the tip element extends farther from a longitudinal axis of the probe than when the tip element is in the first position. In some embodiments, the sleeve is disposable over the probe assembly such that, when the probe assembly is disposed within a patient's tissue, the sleeve is movable relative to the probe assembly to abut the patient's tissue. In some embodiments, the probe includes: an elongated second body extending to the distal end; where the tip element is pivotally coupled to the second body at the distal end; and where translation of the first body relative to the second body along the longitudinal axis of the probe moves the tip element between the first and second positions.

Some embodiments of the present surgical depth gauges further comprise: a sensor configured to capture data indicative of a distance between the distal end of the probe and the sleeve. Some embodiments further comprise: a display configured to display data indicative of data captured by the sensor.

Some embodiments of the present surgical depth gauges further comprise: one or more markings on at least one of the probe assembly and the sleeve, the one or more markings configured to indicate a distance between the distal end of the probe and the sleeve. In some embodiments, the one or more markings are recessed and/or raised relative to the at least one of the probe assembly and the sleeve.

In some embodiments of the present surgical depth gauges, the probe assembly includes: a housing having a proximal end and a distal end; and two or more prongs pivotally coupled to the housing at the distal end, each prong having a tip; where each of the two or more prongs is movable between a retracted position and a deployed position in which the tip of the prong is farther from a longitudinal axis of the probe assembly than when the prong is in the retracted position. In some embodiments, the sleeve is disposable over the probe assembly such that, when the probe assembly is disposed within a patient's tissue, the sleeve is movable relative to the probe assembly to abut the patient's tissue. In some embodiments, each prong of the probe assembly is biased toward the retracted position.

Some embodiments of the present methods (e.g., for measuring the depth of a hole in a bone) comprise: inserting a cannula into the hole, the cannula being disposed around a probe having a proximal end and a distal end including one or more prongs (each being movable between a retracted position and a deployed position in which the prong is farther from a longitudinal axis of the probe than when the prong is in the retracted position; and being biased toward the deployed position); moving the cannula proximally relative to the probe to move the one or more prongs from the retracted position to the deployed position; and engaging a portion of the bone defining the hole with the one or more prongs. Some embodiments further comprise: moving a sleeve disposed around the probe into contact with the bone. Some embodiments further comprise: moving the cannula distally relative to the probe to move the one or more prongs from the deployed position to the retracted position. Some embodiments further comprise: removing the probe from the hole. In some embodiments, the one or more prongs comprise two or more prongs.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, a device or system that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1 is a cross-sectional side view of a first embodiment of the present depth gauges, shown with a probe assembly in a first, retracted position.

FIGS. 2A and 2B are cross-sectional side views of the depth gauge of FIG. 1, shown with the probe assembly in deployed positions.

FIG. 3 is a cross-sectional end view of the probe assembly of FIG. 1, taken along line 3-3, with some components not shown.

FIGS. 4 and 5 are cross-sectional side views of a second embodiment of the present depth gauges, shown with a probe assembly in a first position and a second position, respectively.

FIGS. 6 and 7 are broken cross-sectional side views of a third embodiment of the present depth gauges, shown with a probe assembly in a first position and a second position, respectively.

FIG. 8 is a cross-sectional side-view of a probe assembly that may be suitable for use in some embodiments of the present depth gauges.

FIGS. 9 and 10 are side views of a probe assembly that may be suitable for use in some embodiments of the present depth gauges, shown in a first position and a second position, respectively.

FIGS. 12 and 13 are cross-section views of a probe assembly that may be suitable for use in some embodiments of the present depth gauges, shown in a first position and a second position, respectively.

DETAILED DESCRIPTION

Figure 11:
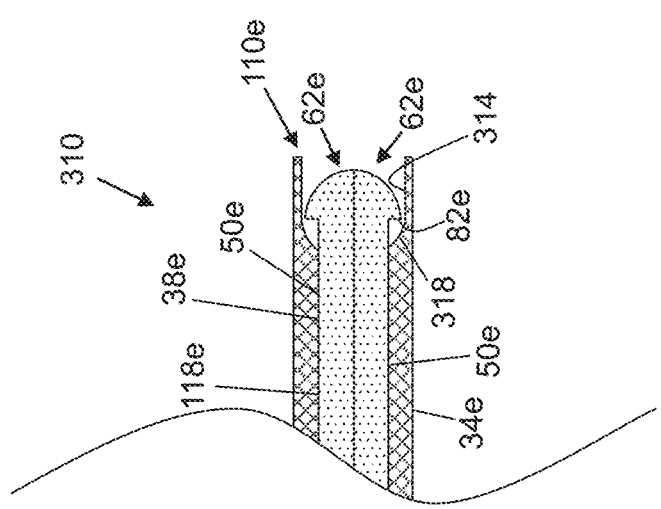
FIG. 11 is a cross-section view of a portion of a sixth embodiment of a probe assembly that may be suitable for use with some embodiments of the present depth gauges.

FIGS. 1-3 depict a first embodiment 10 of the present depth gauges. As described in more detail below, gauge 10 is configured to indicate the depth 14 of a hole 18 in a patient's tissue 22. For example, gauge 10 is configured to measure the depth of a hole in bone tissue and, more specifically, the thickness of cortical bone through which the hole extends. Alternatively or additionally, such tissue 22 can comprise any suitable tissue, such as, for example, connective tissue, muscle tissue, epithelial tissue, and/or the like.

Gauge 10 comprises a probe assembly 26, a sleeve 30 within which the probe assembly 26 is slidably disposed, and a cannula 34 disposed between and slidable relative to the probe assembly and cannula. Probe assembly 26 includes an elongated probe 38 extending between a proximal end 42 and a distal end 46. Distal end 46 of probe 38 is configured to be inserted into a hole 18 in a patient's tissue 22. Distal end 46 of probe 38 includes one or more prongs 50 (e.g., two prongs, as shown). More particularly, probe 38 includes a base 54 extending from proximal end 42 toward distal end 46, and prongs 50 extend from the base to the distal end. Prongs 50 can be coupled to base 54 in any suitable fashion; for example, the base and the prongs may be coupled via one or more fasteners, an interference fit, adhesive, interlocking features of the base and prongs, or can be partially or entirely unitary (i.e., defined by a single, common piece of material).

Probe 38, via prongs 50, is configured to engage a patient's tissue 22 proximate a hole 18 in the patient's tissue once the probe is inserted into the hole. For example, each of prongs 50 includes an arm 58 that terminates in a tip 62. Each tip 62 can be coupled to the respective arm 58 in any suitable fashion; for example, each tip can be coupled to the respective arm via one or more fasteners, an interference fit, adhesive, interlocking features of the tip and arm, or can be partially or entirely unitary (i.e., defined by a single, common piece of material). Each tip 62 includes a protrusion 66 that extends outwardly relative to a longitudinal axis 70 of probe 38. For example, each protrusion 66 can have a maximum transverse dimension 74 that is greater than a corresponding maximum transverse dimension 78 of its respective arm 58. Such protrusions 66 can facilitate prongs 50 engaging a patient's tissue 22 proximate a hole 18 in the patient's tissue once the probe is inserted into the hole and/or mitigate inadvertent removal of the probe from the hole (e.g., when the prongs are in the deployed position, described below).

Protrusion 66 of each tip 62 defines a (e.g., proximally-facing) shoulder 82 configured to increase a surface area of contact between the tip and a patient's tissue 22. For example, when its respective prong 50 is in the retracted position (described below), at least a portion of each shoulder 82 is disposed at an angle 86 relative to longitudinal axis 70 of probe 38. For example, as shown, shoulders 82 are perpendicular to axis 70 when the probe is in the retracted position. Alternatively, angle 86 can be any suitable angle that permits the functionality described in this disclosure, such as, for example, greater than any one of, or between any two: 20, 25, 30, 35, 40, 45, 50, 55, 60, 65, 70, 75, 80, 85, 90, 95, 100, 105, 110, 115, or 120 degrees. Each shoulder 82 can include substantially planar and/or curved (e.g., concave and/or convex) portions.

Distal end 46 of probe 38 includes a rounded (e.g., spherical, ellipsoidal, and/or the like) outer surface 90 configured to reduce the risk of puncturing and/or otherwise undesirably damaging a patient's tissue 22 during insertion of the probe into a hole 18 in the tissue. Outer surface 90 of probe 38 can be at least partially defined by tips 62. For example, tips 62 of prongs 50 can each include a rounded surface 94, and, when the prongs are in the retracted position, the rounded surfaces of the tips can cooperate to define at least a portion of outer surface 90 of probe 38. Rounded surface 94 of each tip 62 can extend from a maximum transverse dimension of the tip to a distal-most point of the tip. In other embodiments, a distal end 46 of a probe 38 can include any suitable outer surface 90, such as, for example, a surface having one or more edges, a surface that tapers to a point, and/or the like.

Portions of probe 38 can comprise a circular cross-section, such as, for example, base 54, prongs 50, and/or the like. For example, and referring to FIG. 3, prongs 50 (e.g., arms 58 and/or their respective tips 62), when in the retracted position, can cooperate to define a circular cross-sectional shape. In other embodiments, portions of the present probes can comprise any suitable cross-section, such as, for example, circular, elliptical, or otherwise rounded, or triangular, square, rectangular, and/or otherwise polygonal.

Prongs 50 of probe 38 are movable between a retracted position (FIG. 1) and a deployed position (FIGS. 2A and 2B) in which tips 62 of the prongs are farther from longitudinal axis 70 of the probe than when the prongs are in the retracted position. When prongs 50 are in the retracted position, the prongs extend in a direction that is substantially parallel to longitudinal axis 70 of probe 38 to facilitate, for example, passage of the probe into a hole 18 in a patient's tissue 22. One or more prongs 50 can be moved to the deployed position to facilitate, for example, engagement of tips 62 with a portion of the tissue that is proximate the hole.

Prongs 50 are biased toward the deployed position. In other words, in the absence of force acting on prongs 50, the prongs will assume the deployed position. For example, in this embodiment, prongs 50 each comprise a resilient material, such as, for example, steel (e.g., spring steel), a polymer (e.g., an elastic polymer), aluminum, and/or the like. In other embodiments, prongs 50 can be biased toward a deployed position by one or more biasing elements, such as, for example, one or more springs, inflatable bladders, wedge-shaped members, and/or the like.

Probe 38 can comprise a biocompatible material, such as, for example, stainless steel, titanium, a ceramic material, a polymer, and/or the like. Probe 38 has a length 98 measured from proximal end 42 to distal end 46. Length 98 can be any suitable length, such as, for example, greater than any one of, or between any two of: 50, 75, 100, 125, 150, 175, 200, 225, 250, 275, 300, 325, 350, 375, 400, 425, 450, 475, or 500 millimeters (mm).

Probe assembly 26 includes a knob 102 coupled to proximal end 42 of probe 38. In this embodiment, knob 102 can be coupled to probe 38 such that the knob is rotationally and/or translationally fixed relative to proximal end 42 of the probe. Knob 102 can be coupled to probe 38 in any suitable fashion, such as, for example, via one or more fasteners, an interference fit, adhesive, interlocking features of the probe and knob, or can be partially or entirely unitary (i.e., defined by a single, common piece of material). Knob 102 can be grasped by a user to, for example, facilitate the user in controlling probe 38, probe assembly 26, and/or gauge 10.

Probe assembly 26 also includes an elongated cannula 34 that extends between a proximal end 106 and a distal end 110 and is configured (e.g., sized) to slidably receive at least a portion of probe 38. For example, cannula 34 can have an inner transverse dimension that is substantially equal to, but slightly larger than, an outer transverse dimension of at least a portion of probe 38. At least a portion of cannula 34 can be transparent or translucent to, for example, facilitate a user in determining a position of probe 38 within the cannula. Cannula 34 can comprise a biocompatible material, such as, for example, one or more of those described above for probe 38. Cannula 34 has a length 114, measured from proximal end 106 to distal end 110, that can be any suitable length, such as, for example, greater than any one of, or between any two of: 50, 75, 100, 125, 150, 175, 200, 225, 250, 275, 300, 325, 350, 375, 400, 425, 450, 475, or 500 mm.

In this embodiment, probe 38 is disposable within cannula 34 such that movement of the cannula proximally and distally relative to the probe causes prongs 50 to move between the deployed and retracted positions, respectively. For example, as cannula 34 is moved proximally relative to probe 38, prongs 50, less restrained by an inner surface 118 of the cannula, are permitted to move from the retracted position toward the deployed position. Similarly, as cannula 34 is moved distally relative to probe 38, prongs 50 are urged by inner surface 118 of the cannula from the deployed position toward the retracted position. When prongs 50 are in the retracted position, prong tips 62, and more particularly, shoulders 82 thereof, abut distal end 110 of cannula 34 (e.g., thereby limiting further distal movement of the cannula relative to probe 38).

Cannula 34 includes a cannula slider 122 that is coupled to probe assembly 26 (e.g., to cannula 34) such that movement of the cannula slider relative to at least one of probe 38 and the cannula moves the cannula relative to the probe. As shown, cannula slider 122 can extend outwardly relative to longitudinal axis 70 of probe 38. In these ways and others, cannula slider 122 can facilitate a user in controlling the position of cannula 34 relative to probe 38 and thus movement of prongs 50 between the retracted and deployed positions.

Gauge 10 comprises a (e.g., rigid) sleeve 30 that extends between a proximal end 130 and a distal end 134 and is disposable over at least a portion of probe assembly 26. More particularly, when probe assembly 26 is at least partially disposed within a patient's tissue 22, sleeve 30 is movable relative to the probe assembly to abut the tissue. At least a portion of sleeve 30 can be transparent or translucent to, for example, facilitate a user in determining a position of probe assembly 26, probe 38, and/or cannula 34 relative to the sleeve. Sleeve 30 can comprise a biocompatible material, such as, for example, one or more of those described above for probe 38. Sleeve 30 has a length 126, measured from a proximal end 130 to a distal end 134, that can be any suitable length, such as, for example, greater than any one of, or between any two of: 20, 25, 30, 35, 40, 45, 50, 55, 60, 65, 70, 75, 80, 85, 90, or 95% of length 98 of probe 38.

Sleeve 30 includes a sleeve slider 138 coupled to sleeve 30 and configured to facilitate a user in controlling the position of the sleeve relative to probe assembly 26, probe 38, and/or cannula 34. For example, sleeve slider 138 can extend outwardly relative to longitudinal axis 70 of probe 38.

Sleeve 30 is configured to permit a user to control the position of cannula 34 relative to probe 38, and thus movement of prongs 50 between the retracted and deployed positions, when the sleeve is disposed over probe assembly 26. To illustrate, sleeve 30 defines a longitudinal slot 142 configured to receive cannula slider 122 when the sleeve is disposed over probe assembly 26. At least via longitudinal slot 142, cannula slider 122 remains accessible to a user to permit the user to move cannula 34 relative to the sleeve and/or probe 38. Longitudinal slot 142 can have a length 146 that is greater than any one of, or between any two of: 20, 25, 30, 35, 40, 45, 50, 55, 60, 65, 70, 75, 80, 85, 90, or 95% of length 126 of the sleeve.

Sleeve 30 is configured to facilitate alignment between cannula 34 and the sleeve and/or to control movement of the cannula relative to the sleeve. For example, sidewalls of longitudinal slot 142, by physically limiting rotational movement of cannula slider 122 within the slot, can limit rotational movement of cannula 34 relative to sleeve 30. For further example, longitudinal slot 142 can include a proximal shoulder 150 and/or distal shoulder 154 configured to physically limit translational movement of cannula slider 122 within the slot and thus translational movement of cannula 34 relative to sleeve 30. Longitudinal slot 142 can be located on sleeve 30 relative to sleeve slider 138 such that, when the sleeve is disposed over probe assembly 26, cannula slider 122 is positioned relative to the sleeve slider to, for example, facilitate user access to both sliders (e.g., with a single hand). For example, when cannula slider 122 is received by longitudinal slot 142, the cannula slider can be angularly disposed relative to sleeve slider 138 about longitudinal axis 70 at an angle that is greater than any one of, or between any two of: 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 degrees.

Gauge 10 is configured to indicate the depth 14 of a hole 18 in a patient's tissue 22. In this embodiment, the depth of a hole in a patient's tissue can correspond to a longitudinal distance 158 between distal end 134 of sleeve 30 and distal end 46 of probe 38, and more particularly, shoulders 82 of prong tips 62. In gauge 10, distance 158 can be indicated by the relative position of a portion of probe 38 and a portion of sleeve 30, a portion of the probe and a portion of cannula 34, a portion of the cannula and a portion of the sleeve, and/or the like. In other gauges (e.g., 10), the depth of a hole in a patient's tissue can correspond to any suitable distance, such as, for example, a distance between a distal end (e.g., 110) of a cannula (e.g., 34) and a distal end (e.g., 46) of a probe (e.g., 38), and such a distance can be indicated by the gauge in any suitable fashion.

Gauge 10 can include one or more markings 162 that are disposed on at least one of probe 38, cannula 34, and sleeve 30 and are configured to indicate distance 158. Such markings 162 can be recessed and/or raised relative to the component on which they are disposed. To illustrate, probe 38 can include markings 162 that are configured to indicate the position of sleeve 30 relative to probe 38 and thus distance 158. More particularly, markings 162 can be disposed on proximal end 42 of probe 38 such that the markings can indicate the position of proximal end 130 of sleeve 30 relative to proximal end 42 of probe 38. Such markings (e.g., 162) can be configured to indicate a distance (e.g., 158) that is within any suitable range, such as, for example, a range that exists between any two of: 2, 4, 6, 8, 10, 12, 14, 16, 18, 20, 25, 30, 35, 40, 45, 50, 60, 70, 80, 90, 100, 125, 150, 175, 200, 225, 250, 275, 300, 325, 350, 375, 400, 425, 450, 475, and 500 mm, at any suitable resolution, such as, for example, a resolution that is greater than any one of, or between any two of: 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, and/or 10 mm (though the markings need not indicate the distance in millimeters).

To illustrate a method of using gauge 10 to determine the depth 14 of a hole 18 in a patient's tissue 22, probe assembly 26 can be inserted into the hole with prongs 50 in the retracted position (e.g., with cannula 34 at its distal-most position relative to probe 38). Probe assembly 26 can be inserted into the hole until prong tips 62 (e.g., shoulders 82 thereof) have moved beyond a distal surface 166 of the tissue (e.g., beyond a distal cortical wall of the bone). Once probe assembly 26 is disposed in the hole, prongs 50 can be moved from the retracted position to the deployed position. For example, a user can hold knob 102, probe 38, and/or sleeve 30 and move cannula 34 proximally relative to the probe (e.g., by applying a force to urge cannula slider 122 in the proximal direction), thereby permitting prongs 50 to move to the deployed position. Probe 38 can then be moved proximally in order to bring shoulders 82 of prong tips 62 into contact with the distal surface of the tissue, as shown in FIG. 2B, thereby reducing the risk of inadvertent removal of the probe from the hole.

Sleeve 30 can then be moved distally relative to probe 38 until distal end 134 of the sleeve engages a proximal surface 170 of the tissue (e.g., a proximal cortical wall of the bone). For example, a user can hold knob 102, probe 38, and/or cannula 34 and (e.g., via operation of sleeve slider 138) move sleeve 30 distally relative to the probe. When prong tips 62 are engaged with the distal surface of the tissue and sleeve 30 is engaged with the proximal surface of the tissue, distance 158 can be determined visually from the position of proximal end 130 of sleeve 30 relative to markings 162.

To remove probe assembly 26 from the hole, prongs 50 can be moved to the retracted position. For example, a user can hold knob 102, probe 38, and/or sleeve 30 and move cannula 34 distally relative to the probe (e.g., by applying force to urge cannula slider 122 in the distal direction), thereby moving prongs 50 to the retracted position.

In other embodiments, gauge 10 can include a sensor 174 configured to capture data indicative of distance 158, which can be coupled to at least one of probe 38, cannula 34, and sleeve 30. Sensor 174 can comprise any suitable sensor, such as, for example, a displacement sensor, a proximity sensor, and/or the like, and such a sensor be magnet-based (e.g., a hall effect sensor, a magnetorestrictive sensor, and/or the like), optical, strain-based (e.g., a strain gauge), and/or the like. To illustrate, a magnet can be coupled to a first component (e.g., probe 38, cannula 34, and/or sleeve 30) and/or at least a portion of the first component can be magnetic, and a hall effect sensor 174 can be coupled to a second component (e.g., probe 38, cannula 34, and/or sleeve 30) that is movable relative to the first component such that the sensor can capture data indicative of the position of the magnet relative to the sensor and thus the position of the first component relative to the second component. For example, gauge 10 can include a display 178 (e.g., a liquid crystal display (LCD), a light-emitting diode (LED) display, and/or the like) configured to display distance 158. As shown, display 178 can be coupled to at least one of sleeve 30 and probe assembly 26 (e.g., to knob 102).

Referring now to FIGS. 4 and 5, shown is a second embodiment 182 of the present depth gauges. In this embodiment, components that are similar in structure and/or function to those discussed above are labeled with the same reference numerals and a suffix "a."

Gauge 182 includes a probe assembly 186 having threaded components for moving prongs 50a between a retracted position (FIG. 4) and a deployed position (FIG. 5). To illustrate, probe assembly 186 can include a threaded shaft 190 that is threadably engaged with cannula 34a (e.g., at inner surface 194) such that rotation of the shaft relative to the cannula causes translation of the cannula relative to the shaft. Knob 102a can be (e.g., fixedly) coupled to shaft 190 such that, for example, a user can rotate the knob relative to cannula 34a, thereby translating the cannula relative to the knob. In order to prevent translation of probe 38a relative to shaft 190 during translation of cannula 34a relative to the shaft, the probe can be translationally fixed relative to the shaft. To illustrate, proximal end 42a of probe 38a can be coupled to knob 102a via, for example, an anchor 198. Thus, as knob 102a is rotated relative to cannula 34a, the cannula may translate relative to probe 38a.

Probe assembly 186 can be configured such that probe 38a is rotatable relative to shaft 190. For example, probe 38a can be rotatably received within a bore 202 of shaft 190. For further example, anchor 198 can be rotatably disposed within knob 102a, which may be facilitated by one or more bearings, bushings, and/or the like disposed between the anchor and the knob. Thus, as shaft 190 is rotated relative to cannula 34a to translate the cannula relative to the shaft, rotation of the probe with the shaft, which might otherwise complicate obtaining depth measurements using probe assembly 186, may be limited.

Sleeve 30a can be configured to limit rotation of cannula 34a with shaft 190 during rotation of the shaft. For example, cannula slider 122a of cannula 34a can be received within longitudinal slot 142a of sleeve 30a. In at least this way, a user can hold sleeve 30a during rotation of shaft 190 to prevent rotation of cannula 34a with the shaft, thereby facilitating translation of the cannula relative to the shaft.

To illustrate, a user may hold sleeve 30a and rotate knob 102a in a first direction to move cannula 34a proximally relative probe 38a, thereby permitting prongs 50a to move toward the deployed position. Similarly, a user may hold sleeve 30a and rotate knob 102a in a second direction that is opposite to the first direction to move cannula 34a distally relative to probe 38a, thereby urging prongs 50a toward the retracted position.

Referring now to FIGS. 6 and 7, shown is a third embodiment 206 of the present gauges. In this embodiment, components that are similar in structure and/or function to those discussed above are labeled with the same reference numerals and a suffix "b."

Gauge 206 includes probe assembly 210 having a retractable pen-like mechanism for moving one or more prongs 50 between a retracted position (FIG. 6) and a deployed position (FIG. 7). For example, in probe assembly 210, probe 38b can include a protrusion 214 disposed on an outer surface 90b of the probe. Cannula 34b can include a plurality of alternating retraction catches 218 (e.g., grooves) and deployment catches 222 (e.g., grooves) disposed circumferentially around an inner surface 118b of the cannula, each configured to removably and/or releasably receive protrusion 214 of probe 38b. Retraction catches 218 can extend proximally beyond deployment catches 222 such that, for example, probe 38b is disposed farther proximally relative to cannula 34b when protrusion 214 is received within a retraction catch than when the protrusion is received within a deployment catch. Cannula 34b can define a sloped surface 226 between adjacent catches, which can assist in guiding protrusion 214 between the catches. To illustrate, when protrusion 214 is received within a retraction catch 218, prongs 50 of probe 38b may be in the retracted position, and when the protrusion is received within a deployment catch 222, the prongs may be in the deployed position.

Probe assembly 210 can include a biasing member 230 (e.g., a spring) configured to bias probe 38b in a proximal direction relative to cannula 34b, thereby maintaining protrusion 214 of the probe in a retraction catch 218 or a deployment catch 222 of the cannula and thus prongs 50 of the probe in the retracted position or the deployed position, respectively.

Knob 102b of probe assembly 210 can include a plurality of teeth 234 configured to engage a plurality of teeth 238 disposed on distal end 42b of probe 38b. Knob 102b can be translationally movable and rotationally fixed relative to cannula 34b, via, for example, a protrusion of one of the knob and the cannula received within a slot of the other and the knob and the cannula. Teeth 234 of knob 102a and teeth 238 of probe 38b can be triangular, and, when protrusion 214 is received within a retraction catch 218 or a deployment catch 222, teeth 234 can be rotationally offset relative to teeth 238, such that, for example, when teeth 234 engage teeth 238, probe 38b is urged to rotate relative to knob 102b, which can facilitate movement of the protrusion between adjacent retraction and deployment catches.

To illustrate, knob 102b can be moved distally relative to cannula 34b, and, via engagement between teeth 234 of the knob and teeth 238 of probe 38b, the probe can be moved distally relative to the cannula. As protrusion 214 of probe 38b moves out of a deployment catch 222 or a retraction catch 218, the protrusion can be guided by sloped surface 226 and/or urged by engagement of teeth 234 and teeth 238 to an adjacent one of the catches, thereby moving prongs 50 of probe 38b between the retracted and deployed positions.

Referring now to FIG. 8, shown is a further embodiment 242 of the present probe assemblies that may be suitable for use in some embodiments of the present gauges. In this embodiment, components that are similar in structure and/or function to those discussed above are labeled with the same reference numerals and a suffix "c."

Probe assembly 242 includes a scissor-like mechanism for moving one or more prongs 50c between a retracted position and a deployed position. Probe assembly 242 can include a hinge 246 configured to facilitate movement of prongs 50c between the retracted and deployed positions. For example, hinge 246 can be coupled to each prong 50c such that the prong is rotatable about the hinge between the retracted and deployed positions. Prongs 50c are biased toward the deployed position, via, for example, a biasing member 250 (e.g., a spring). For example, biasing member 250 is configured to exert a force on proximal ends 254 of prongs 50c such that the prongs are urged to rotate about hinge 246 toward the deployed position.

Probe assembly 242 includes a housing 258 defining an interior volume 262. Probe 38c is disposed within interior volume 262 of housing 258 such that prongs 50c extend from a distal end of the housing. In at least this way, housing 258 (e.g., a sidewall thereof) can physically limit movement of prongs 50c beyond the deployed position. As shown, hinge 246 can be disposed within and/or coupled to the housing. Housing 258 defines one or more openings 266 in communication with interior volume 262, each configured to allow a user to proximal end 254 of a prong 50c to move the prong between the retracted and deployed positions. To illustrate, a user, via openings 266, may exert a force on proximal ends 254 of prongs 50c that is sufficient to overcome a force applied to the prongs by biasing member 250, thereby rotating the prongs about hinge 246 toward the retracted position. When released by the user, prongs 50c may, via biasing member 250, return to the deployed position.

Referring now to FIGS. 9 and 10, shown is a further embodiment 270 of the present probe assemblies that may be suitable for use in some embodiments of the present gauges. In this embodiment, components that are similar in structure and/or function to those discussed above are labeled with the same reference numerals and a suffix "d."

Probe assembly 270 includes a probe 274 that has an elongated first body 278 extending to distal end 282 of the probe and a tip element 286 that is pivotally coupled (e.g., via a pin) to the first body at the distal end. Tip element 286 is movable relative to first body 278 between a first position (e.g., a retracted position, as shown in FIG. 9) and a second position (e.g., a deployed position, as shown in FIG. 10) in which the tip element extends further from longitudinal axis 290 of probe 274 than when the tip element is in the first position. To illustrate, tip element 286 has a length 294 and a width 298 that is smaller than the length such that, as the tip element is rotated relative to first body 278, the distance that the tip extends from longitudinal axis 290 of probe 274 is varied.

Movement of tip element 286 relative to first body 278 can be accomplished in any suitable fashion. For example, probe 274 has a second elongated body 302 extending to distal end 282 that is pivotally coupled (e.g., via a pin) to tip element 286 at the distal end. At least via pivotal coupling of first body 278 and second body 302 to tip element 286, translation of the first body relative to the second body along longitudinal axis 290 of probe 274 can move tip element 286 between the first and second positions.

Probe 274 can be configured such that, when tip element 286 is in the first position, a maximum transverse dimension of the probe is minimized to, for example, facilitate insertion of the probe into a hole 18 in a patient's tissue 22. For example, one of first body 278 and second body 302 can be pivotally coupled to tip element 286 at a slot 306, which can allow for an increased range of movement of the tip element relative to the at least one body.

Referring now to FIG. 11, shown is a further embodiment 310 of the present probe assembles that may be suitable for use in some embodiments of the present gauges. In this embodiment, components that are similar in structure and/or function to those discussed above are labeled with the same reference numerals and a suffix "e."

As shown, probe assembly 310 includes a cannula 34e having a distal end 110e that extends longitudinally beyond at least a portion of prong tips 62e (e.g., shoulders 82e thereof) of probe 38e when the prongs are in a retracted position. For example, inner surface 118e of cannula 34e includes a recess 314 at distal end 110e, which is configured to receive at least a portion of prong tips 62e when prongs 50e are in the retracted position. Recess 314 can prevent undesirable movement of prongs 50 relative to cannula 34e and/or facilitate retention of the prongs in the retracted position. For example, recess 314 can include a curved surface 318 configured to engage prong tips 62e, thereby preventing further proximal movement of prongs 50 relative to cannula 34e and/or urging the prongs toward the retracted position. In other embodiments, a recess (e.g., 314) can include a substantially planar surface (e.g., 318) configured to engage one or more shoulders (e.g., 82e) of prong tips (e.g., 62e), and/or the like.

Referring now to FIGS. 12 and 13, shown is a further embodiment 322 of the present probe assemblies that may be suitable for use in some embodiments of the present gauges.

Probe assembly 322 includes a housing 326 comprising one or more openings 330 at a distal end 334 of the housing. Probe assembly 322 includes two or more prongs 338 (e.g., two prongs as shown), each of which are pivotally coupled (e.g., via a pin 342) to housing 326 such that the pin is configured to, at least in part, facilitate movement of the prongs between a retracted position (e.g., FIG. 12) and a deployed position (e.g., FIG. 13) through openings 330. For example, in this embodiment, one or more prongs 338 are shaped such that, when the prongs are in the deployed position, an inner surface 344 of each prong is substantially perpendicular to a longitudinal axis 346 of probe assembly 322.

Probe assembly 322 includes an actuation member 350 having an elongated shaft 354 and a distal portion 358 configured to define a slot 362. Actuation member 350 is configured to move one or more prongs 338 between the retracted and deployed positions. To illustrate, each prong 338 includes a guide pin 366 movable in slot 362 such that, for example, longitudinal movement of the actuation member relative to housing 326 moves the prongs between the retracted and deployed positions. In some embodiments, actuation member 350 can be longitudinally biased (e.g., by a biasing member, such as, for example, a spring) toward distal end 334 of housing 326 such that the actuation member biases prongs 338 toward the retracted position and longitudinal movement of the actuation member against the biasing force can cause the prongs to move toward the deployed position.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A surgical depth gauge comprising:
a probe assembly including:
 a probe having a proximal end and a distal end that includes a first transverse dimension, the distal end including one or more prongs, each of the one or more prongs:
  having a distal-most tip;
  being movable between a retracted position and a deployed position in which the tip of the one or more prongs is farther from a longitudinal axis of the probe than when the one or more prongs is in the retracted position; and
  being biased toward the deployed position; and
 a cannula having a proximal end and a distal end that includes a second transverse dimension;
 where:
  the probe is disposable within the cannula such that moving the distal end of the probe toward and away from the distal end of the cannula causes each of the one or more prongs to move between the retracted and deployed positions; and
  while the one or more prongs is in the retracted position, the first transverse dimension is greater than or equal to the second transverse dimension such that the distal end of the probe is disposed outside the distal end of the cannula in the retracted position; and
a sleeve defining a passageway configured to receive the probe and the cannula such that, when the probe assembly is disposed within a patient's tissue, the sleeve is movable relative to the probe assembly to abut the patient's tissue.

2. The surgical depth gauge of claim 1, where the one or more prongs comprises two or more prongs.

3. The surgical depth gauge of claim 2, where the tip of each of the prongs defines a shoulder that abuts the distal end of the cannula when the prong is in the retracted position.

4. The surgical depth gauge of claim 1, comprising a slider coupled to the probe assembly such that movement of the slider relative to at least one of the probe and the cannula moves the cannula relative to the probe.

5. The surgical depth gauge of claim 1, where:
the probe is movable relative to the cannula between a first position in which each of the one or more prongs is in the retracted position and a second position in which each of the one or more prongs is in the deployed position.

6. The surgical depth gauge of claim 1, where at least one of the one or more prongs comprises a resilient material.

7. A surgical depth gauge comprising:
a probe assembly including:
 a probe having a unitary body that includes a proximal end and a distal end, the distal end including two or more prongs, each of the two or more prongs:
  having a distal-most tip;
  being movable between a closed position and an open position in which the tip of the two or more prongs is farther from a longitudinal axis of the probe than when the two or more prongs is in the closed position; and
  being biased toward the open position; and
 a cannula having a proximal end and a distal end;
 where:
  the probe is disposable within the cannula such that moving the distal end of the probe toward and away from the distal end of the cannula causes each of the two or more prongs to move between the closed and open positions;

a sleeve disposable over at least a portion of the probe and the cannula such that, when the probe assembly is disposed within a patient's tissue, the sleeve is movable relative to the probe assembly to abut the patient's tissue; and while the probe is disposed within the cannula, at least a portion of the probe is disposed within both the cannula and the sleeve.

8. The surgical depth gauge of claim 7, where, while the probe is disposed within the cannula, the proximal and distal ends of the probe are disposed outside the cannula.

9. The surgical depth gauge of claim 7, further comprises a knob coupled to the proximal end of the probe such that movement of the knob moves the probe relative to the cannula.

10. The surgical depth gauge of claim 7, where:
   a first portion of the distal end of the probe includes a first transverse dimension;
   a second portion the distal end of the probe includes a second transverse dimension;
   the cannula defines a passage having a third transverse dimension; and
   the first transverse dimension is greater than or equal to the second transverse dimension and the third transverse dimension such that the first portion of the distal end of the probe is disposed outside the passage of the cannula when the two or more prongs are in the closed position and the second portion of the distal end of probe is disposed within the passage.

11. The surgical depth gauge of claim 7, where:
   the probe is movable along the longitudinal axis relative to the cannula between a retracted position in which each of the two or more prongs are in the closed position and an extended position in which each of the two or more prongs are in the open position; and
   the distal end of the probe is closer to the distal end of the cannula in the retracted position than in the extended position.

\* \* \* \* \*